(12) United States Patent
Stauber

(10) Patent No.: US 8,894,659 B2
(45) Date of Patent: Nov. 25, 2014

(54) SPINAL SURGERY DISTRACTION WITH AN INTEGRATED RETRACTOR

(75) Inventor: Marshall Ephraim Stauber, Hollywood, FL (US)

(73) Assignee: Globus Medical, Inc., Audubon, PA (US)

(*) Notice: Subject to any disclaimer, the term of this patent is extended or adjusted under 35 U.S.C. 154(b) by 0 days.

(21) Appl. No.: 13/335,273

(22) Filed: Dec. 22, 2011

(65) Prior Publication Data

US 2012/0095474 A1    Apr. 19, 2012

Related U.S. Application Data

(63) Continuation of application No. 11/163,018, filed on Oct. 3, 2005, now Pat. No. 8,105,331.

(51) Int. Cl.
  *A61B 1/32*  (2006.01)
  *A61B 17/56* (2006.01)
  *A61F 2/46*  (2006.01)
  *A61B 17/02* (2006.01)

(52) U.S. Cl.
  CPC .............. *A61B 17/025* (2013.01); *A61B 17/02* (2013.01); *A61B 2017/0256* (2013.01)
  USPC ........................................... 606/90; 600/201

(58) Field of Classification Search
  USPC ............ 600/201, 235; 606/86 A, 90, 99, 105, 606/190
  See application file for complete search history.

(56) References Cited

U.S. PATENT DOCUMENTS

| | | | | |
|---|---|---|---|---|
| 4,597,385 A  * | 7/1986 | Watson | ...... | 600/564 |
| 5,645,519 A  * | 7/1997 | Lee et al. | ...... | 600/114 |
| 6,224,599 B1 * | 5/2001 | Baynham et al. | ...... | 606/90 |
| 8,105,331 B2 * | 1/2012 | Stauber | ...... | 606/90 |
| 2004/0059318 A1 * | 3/2004 | Zhang et al. | ...... | 606/1 |

* cited by examiner

*Primary Examiner* — Christian Sevilla

(57) ABSTRACT

A spinal surgery retractor with a slotted keyway for integrating a keyed spinal distractor. This retractor and distractor combination slide together to displace a portion of the intervertebral disk space to restore or maintain intervertebral spacing and facilitate retraction of surrounding soft tissues while disk space surgery is performed. The distractor head and mating portion of the retractors have matching profiles that enable the retractor to maintain distraction of the vertebra after removal of the distractor portion of the tool, permitting access to increase at the operating site. The retractor has convex curved surfaces that interface with a majority of retracted soft tissues during progression of the retraction process, which enhance retractor safety. In addition, the retractor portion of the tool has a proximally located section that is laterally flexible, which provides further progression in the retraction process while increasing relative access to the operating site.

12 Claims, 8 Drawing Sheets

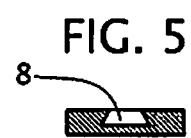
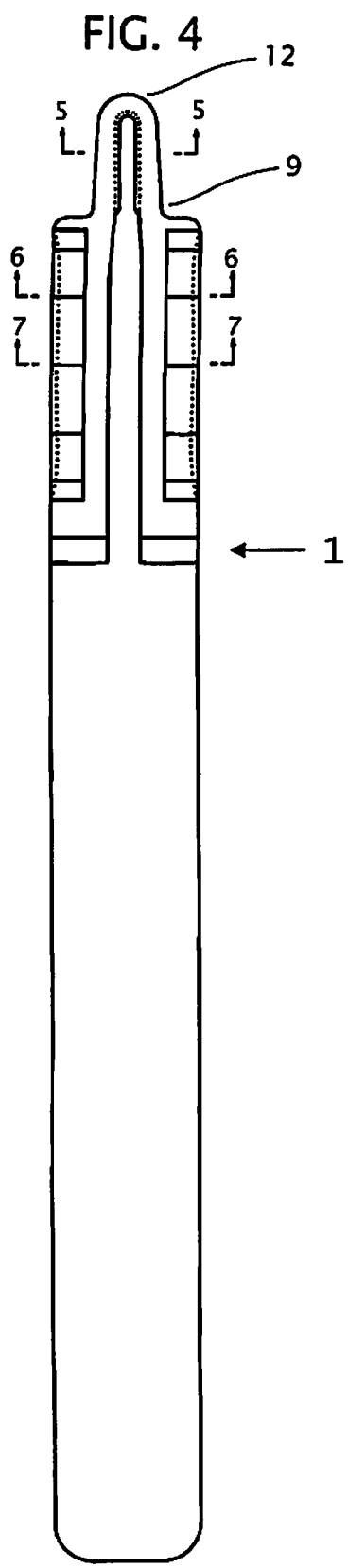

SPINAL SURGERY DISTRACTION WITH AN INTEGRATED RETRACTOR

CROSS REFERENCE TO RELATED APPLICATIONS

This application is a continuation application of U.S. patent application Ser. No. 11/163,018 entitled "SPINAL SURGERY DISTRACTION WITH AN INTEGRATED RETRACTOR," filed on Oct. 3, 2005 now U.S. Pat. No. 8,105,331, the entire disclosure of which is incorporated herein by reference.

BACKGROUND OF THE INVENTION

1. Field of Invention

This invention generally relates to the field of surgical appliances for disk space spinal surgery, specifically retractors and distractors that are used to facilitate retraction of soft tissue surrounding the disc space, and the management intervertebral spacing in disc space surgery with a distraction device.

2. Prior Art

Surgery involving spinal disc space operations that require open access through an incision usually necessitate a means to hold the incision open without injury to retracted tissue while the surgeon operates on the diseased or injured portion of the spine. This retraction reduces the required size of the surgical incision, contributing to improved visualization of pathology, while decreasing surgical risk factors. In addition to this, disc space surgical procedures often require a means to stabilize and maintain intervertebral spacing via a distraction device for the disc space being operated on.

Few retractors used in disk space surgery incorporate a distraction device to maintain intervertebral spacing. Those that do, incorporate a distractor that is usually cumbersome, and bulky and often requires drilling. One example of a device of similar function is the retractor-distractor device within U.S. Pat. No. 5,944,658. Like this example, most spinal retractors for open access surgery that incorporate a distractor are typically complex, awkward, time consuming to set up, and are usually comparatively difficult work with when there is a need to quickly modify apparatus position, distraction within new position, and degree of retraction, when compared to dedicated devices.

OBJECTS AND ADVANTAGES OF THE INVENTION

The present invention offers several advantages over existing devices used in the art. Some of these advantages are:

(a) The present invention enables the direct placement of a retractor attached to a distractor to maintain soft tissue distraction without the need for an individual holding the retractor blade and maintaining pressure on the soft tissues. This provides the surgeon with enhanced control of the soft tissue retraction process, thereby reducing the chances of necrosis of the soft tissue.

(b) The distractor retractor assembly also reduces the chances of soft tissue coming out from underneath the retractor due to the fact that a portion of the retractor extends down into the disk space. This is particularly important, as once portions of the vertebral disk have been removed, the resulting void presents a space for soft tissue such as blood vessels and nerves to enter, increasing the chances for soft tissue damage during final removal of disk space material and/or placement of implants, i.e., total disk replacements or vertebral interbody fusions.

(c) The ability to have a retractor which has a proximal flexible portion, allowing one to bend this portion of the retractor away from the operating field, resulting in an increase of the amount of exposure and light that can be brought into the operating field, improving the quality of the exposure. Everything that can be done to improve the quality of operating field exposure with less risk to the soft tissue minimizes the overall risks of the surgery.

(d) The integration of a distractor head with the retractor allows for maintenance of the disk height during removal of the disk material, which tends to collapse as the disk material is removed. This is possible since successive replacement of the distraction portion of the assembly is enabled via the keyway and slot on the retractor. This characteristic of the invention aids in the gradual progression of distraction. Thus, providing control of distraction while giving a much better visualization of the soft tissue within the disk as well as improving access for the removal of any disk herniated fragments from behind the disk space.

(e) Surgical distraction of vertebra and retraction of adjacent soft tissue can be maintained by the retractor after the distractor integrated with its retractor has accomplished initial distraction. Thus allowing subsequent removal of the distractor tool from the retractor keyway and the operating site after the initial distraction. This provides retraction with a comparative increase in access to the operating site when distraction and retraction are coincident surgical requirements. This can be followed with incremental distraction changes by exchanging the distractor portion of the assembly and/or alternately changing distractor-retractor assemblies laterally.

Further advantages will become apparent from a consideration of the following description and drawings.

SUMMARY OF THE INVENTION

The present invention is broadly directed toward a spinal distractor that is combined with a retractor, for use in lumbar, thoracic, and cervical disc space surgery. At this time, the preferred usage of the invention involves lumbar spine surgical procedures of the disk space and vertebral distraction at the L5-S1, L4-L5, L3-L4, and L2-L3 levels via a retroperitoneal approach anteriorly with retraction of adjacent soft tissue.

The present invention consists of two major parts of an integrated assembly that is used as a spinal surgery retractor and distractor. The distractor portion of the invention has a distractor head or plug incorporating a keyed shape on its face that mates to a portion of the retractor via a keyway in the distal end of the retractor. This mating portion of the retractor has a profile that matches or is similar to the profile of the distractor head. The distractor head has a rod fastened to it, preferably using machine screw threads that provide a means to apply insertion force to the entire assembly, and removal force to the distractor portion of the assembly.

Once the distractor is engaged with the retractor through its keyway, the shape of the retractor keyway does not allow the distractor to slide ahead of the retractor. This enables the distractor to apply insertion force to the entire assembly to enable progression into the incision, followed by insertion of the distal tip of the entire assembly into a portion of the disc space, with most or all of the insertion force applied to the distractor.

A slot adjacent to the retractor keyway enables removal of the distractor from the retractor after insertion of the assembly into the operating site, allowing for an increase of exposure in the operating field, and for minute changes in distraction by exchanging the distraction portion of the assembly. After the assembled distractor and retractor are inserted into the operating site, the retractor can be used to maintain distraction at the operating site by employing its distal end profile (described above).

The retractor has a thinned or blade shaped proximal end to allow for flexibility of its proximal portion, enabling further progression of retraction and permitting increased access to the operating field. In addition, the retractor has convex curved surfaces that interface with a significant amount of retracted soft tissue during progression of the retraction process, which contributes towards retractor safety. The portion of the retractor tool described above as 'thinned or blade shaped', is formed at the opened end of the above-described slot by abruptly tapering to a uniform thickness which extends uniformly to the proximal edge of the surgical tool.

BRIEF DESCRIPTION OF THE DRAWINGS

Figures

FIG. 4 shows an orthogonal top view of the retractor with hidden lines illustrating the extent of the distal end keyway and portions of the soft-tissue-interfacing convex surfaces.

FIG. 5 is a cross sectional view of the distal tip of the retractor, showing one orthogonal view pointing into the retractor keyway.

FIG. 6 is a cross sectional view of the distal portion of convex surfaces on the retractor and orthogonal view pointing into the slot that is adjacent to the keyway.

FIG. 7 is a cross sectional view of the middle portion of the convex surfaces on the retractor and the middle of the slot that is adjacent to the keyway.

DRAWINGS

Reference Numerals

Listing 1-12

Figure 1:
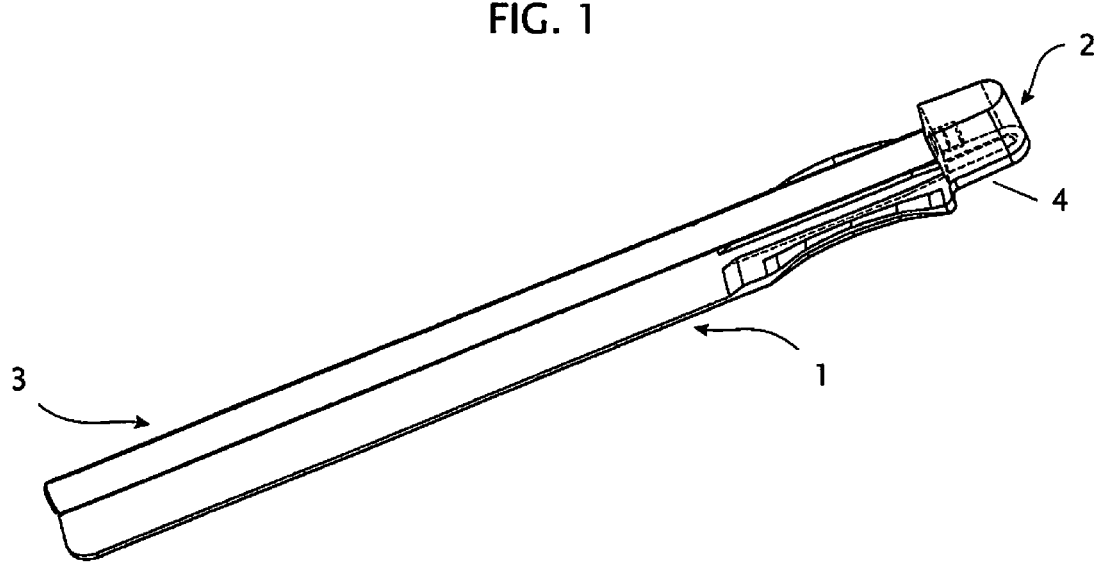
FIG. 1 shows the distractor tool combined with the retractor, with the lengthwise edge of the retractor exposed.

11 retractor 2 distractor head 3 distractor rod 4 retractor distal tip 5 flexible section of retractor 6 taper to flexible section 7 retractor convex curves 8 retractor keyway 9 starting point of retractor 10 slot adjacent to keyway matching-profile 11 keyed portion of the 12 end point-matching profile distractor head

DETAILED DESCRIPTION OF THE REFERRED EMBODIMENT

Figure 2:
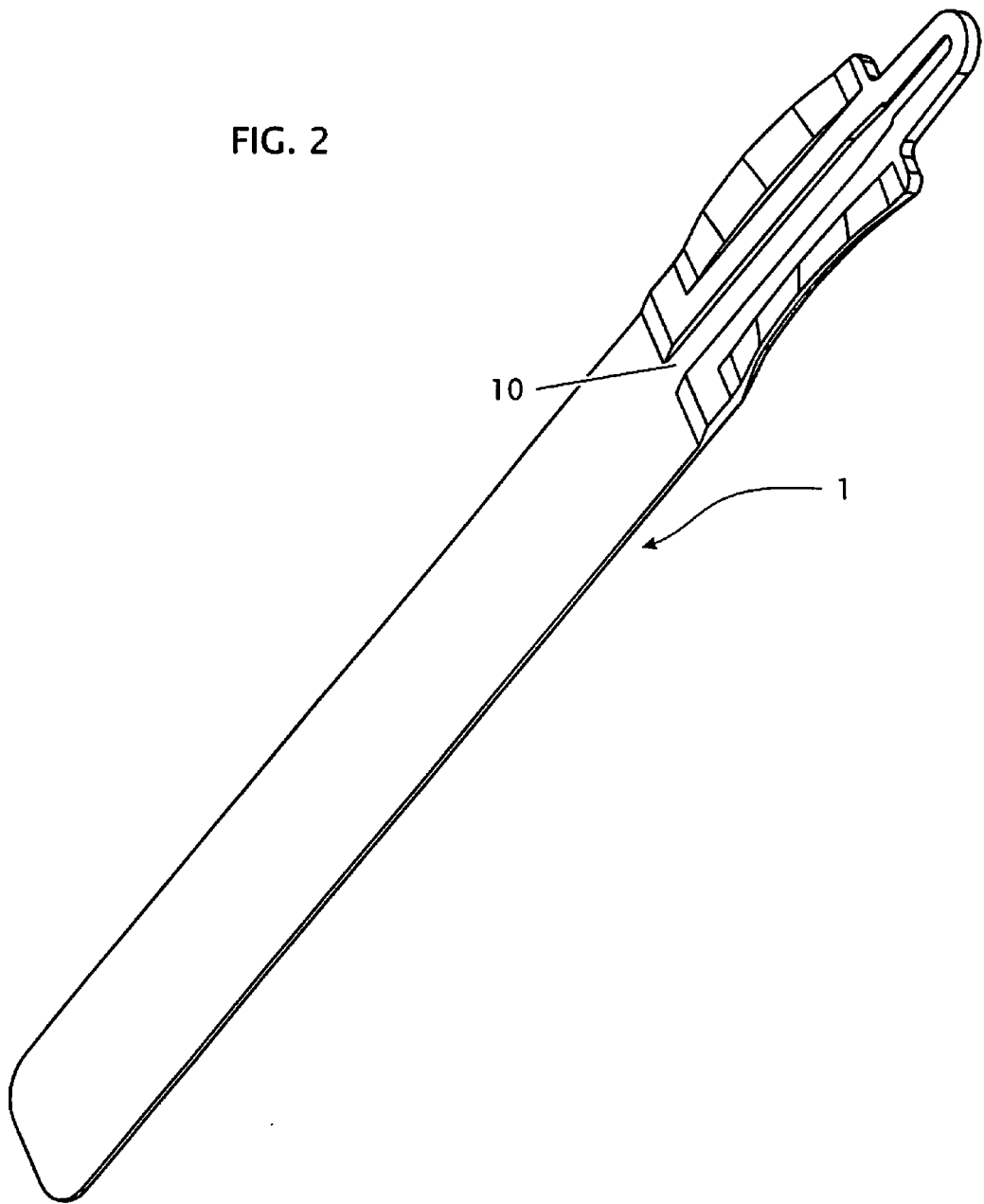
FIG. 2 shows the retractor without its distractor, with the keyway, matching profile and slot adjacent to the keyway exposed with reference number 10.

The preferred embodiment of the present invention with all its parts integrated is illustrated in FIG. 1. Within this figure the retractor 1 is shown with the distractor head 2 engaged with the distal tip of the retractor 4 (shown in proportion with a 14 mm wide distal tip). The distractor head 2 is fastened together with distractor rod 3 with machine screw threads. With the distractor portion of the assembly removed as shown in FIG. 2, the slot 10 of the retractor portion of the invention that enables removal of the distrator head is visible.

Figure 3:
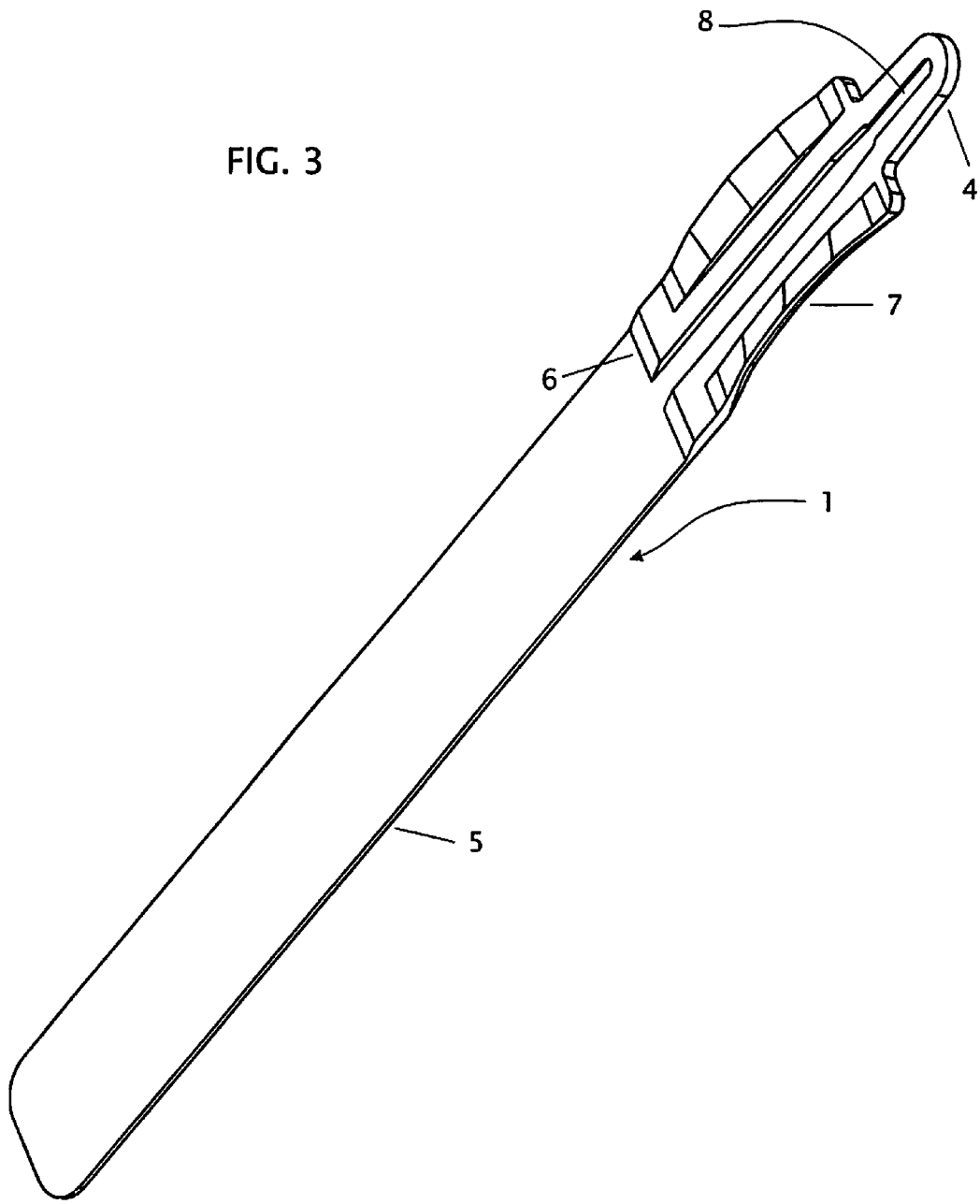
FIG. 3 shows the retractor with corresponding reference numerals.

Similarly, FIG. 3 details other features of the retractor that are visible when the distractor portion of the assembly is removed. The detail shown in FIG. 3 illustrates the distal tip of the retractor, which has a profile that matches the profile of the distractor head, and is indicated as feature reference 4 (shown in proportion with a 14 mm wide profile). This feature incorporates the retractor keyway 8 on the face that mates with the distractor head 2 {shown in FIG. 1}. The keyway 8 extends and opens to the slot 10 shown on FIG. 2.

Continuing further from the distal tip and on the broad side opposite of the slot 10 (FIG. 2) of the retractor as shown in FIG. 3, is a feature referenced as 7, which shows the convex surfaces that interface with soft tissue. In FIG. 3 shown, indicated by feature reference number 6 is an abrupt taper. This taper ends at the feature referenced as 5, resulting in a usable flexibility of the proximal portion that is shown as feature 5 within FIG. 3. Feature 5 has been previously described in the summary as 'thinned or blade shaped' and thus, the retractor portion of the assembly can be alternately described as a retractor blade, although it is much more intricate and functional than a simple blade structure.

Figure 8:
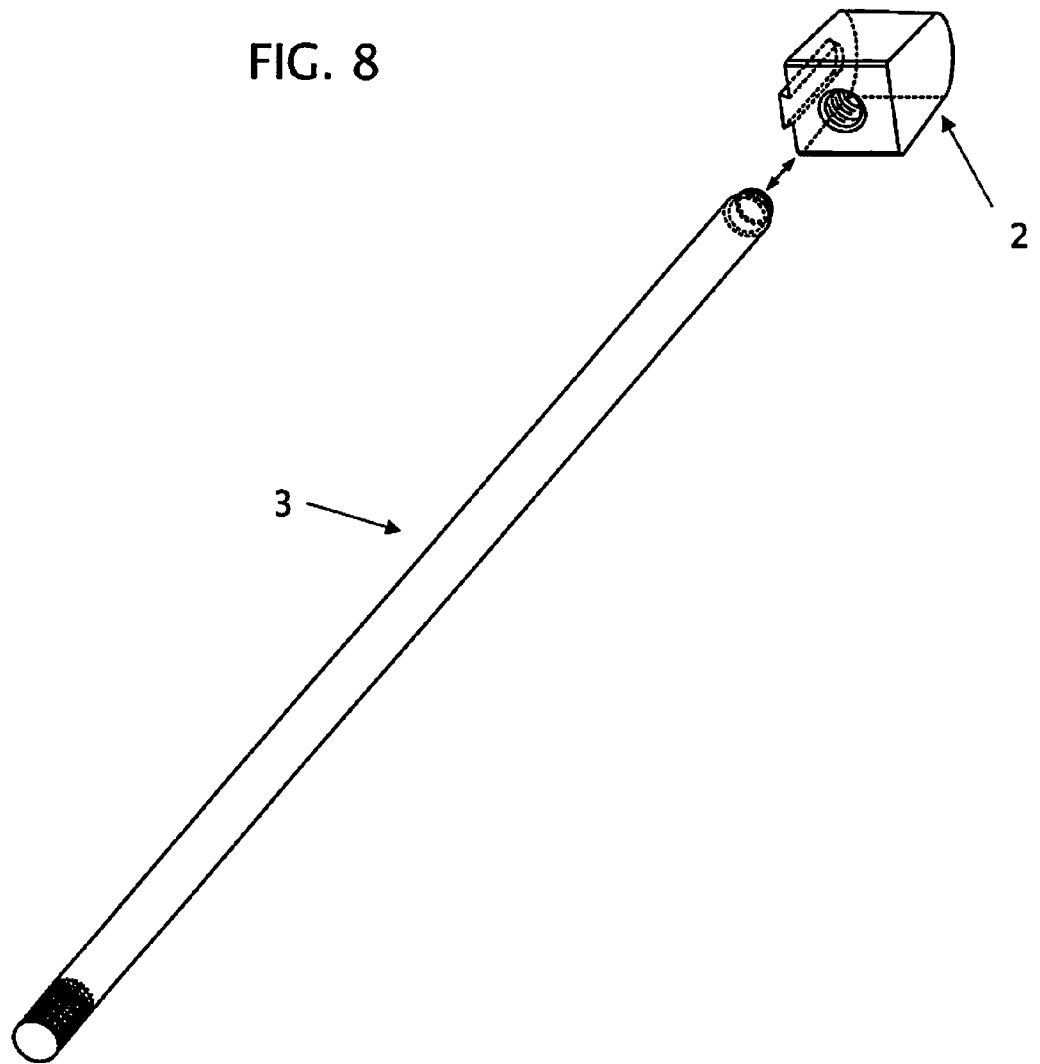
FIG. 8 shows the distractor head and distractor rod separated, with hidden lines illustrating the extent of the keyed portion of the distractor head and machine screw threads on the distractor rod.

FIG. 4 also illustrates a view of the retractor (retractor blade structure) without the distractor portion of the assembly. This view of the retractor shows the extent of the distal tip of the retractor, which incorporates the profile that matches the distractor head profile (FIGS. 1 and 8 ref. #2) using feature reference numbers 9 and 12 as limits. This view of the distal tip of the retractor also shows the extent of the hidden portion of the keyway between feature reference numbers 9 and 12 (shown in proportion with a 14 mm wide distal tip profile). In addition, FIG. 4 also references cross sections of the retractor depicted in FIGS. 5, 6, and 7.

The illustration in FIG. 5 shows an enlarged view of the cross section of the distal tip of the retractor. This figure shows the cross sectional shape of the retractor keyway 8. Additionally, the keyway 8 sectional view in FIG. 5 shows a beveled shape, which enables the keyway 8 to retain the distractor head 2 {shown in FIG. 1} when its keyed face is slid into the retractor keyway 8.

The cross section of the distal portion of the slot adjacent to the retractor keyway (top of illustration) and the distal convexly curved surfaces (bottom of illustration) that interface with soft tissue—are shown in FIG. 6. The middle cross section of the same type of surfaces is shown in FIG. 7.

Figure 9:
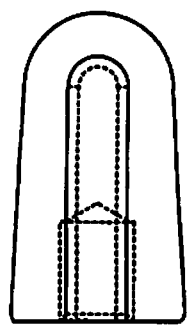
FIG. 9 shows an orthogonal view of the distractor head with the matching profile and keyed portion facing out.
Figure 10:
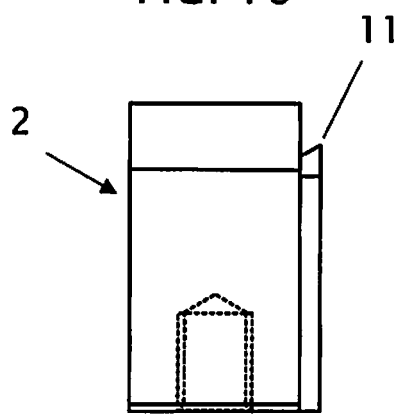
FIG. 10 shows an orthogonal view of the side of the distractor head with a side view of the keyed portion of the distractor.
Figure 11:
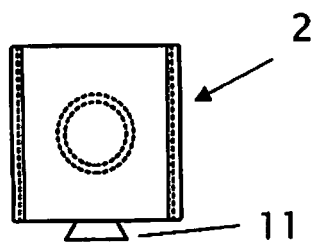
FIG. 11 shows an orthogonal view of the distal end of the distractor head.

An orthogonal view of the distractor head with the matching profile and keyed section facing out is illustrated in FIG. 9. The hidden lines within this figure show the interface of the keyed section of the distractor head and its matching profile, as well as an example of the extent of the distractor rod fastening hole. Also note that the distal end of the keyed section (shown in FIG. 9) is round and matches the distal end of the retractor keyway 8. This feature creates an interface, that when slid together with the retractor keyway, prevents the distractor from sliding in advance of the retractor. FIGS. 10 and 11 are orthogonal views from the side and distal end of the distractor head with further detail of the keyed section.

Figure 12:
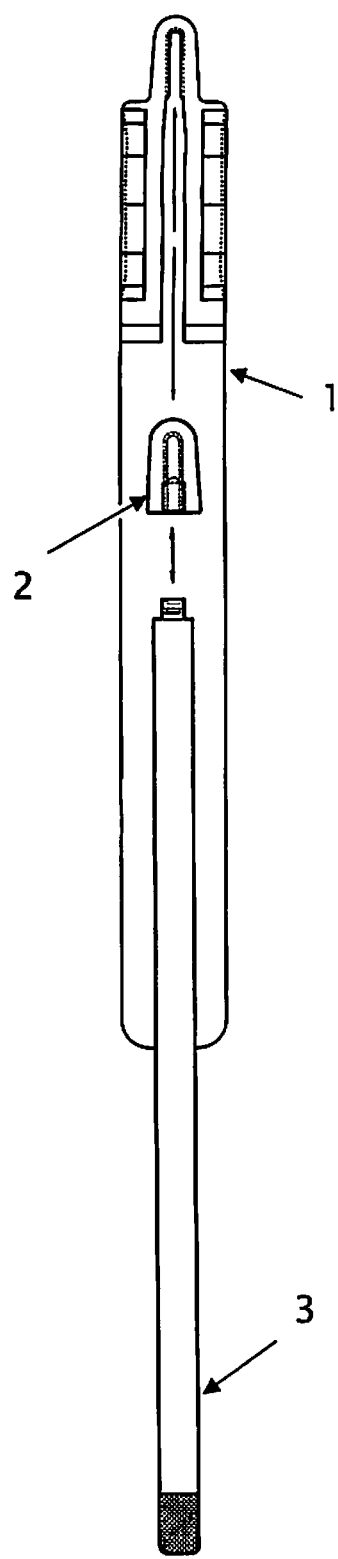
FIG. 12 is a top view of the retractor, distractor head, and distrator rod, with the direction of placement indicated for integration.

The organization of the complete assembly is illustrated in FIG. 12. As shown in this figure, the distrator rod 3 is fastened to the distractor head 2 and this distractor tool assembly is slid into the retractor in the direction indicated until the retractor keyway stops the sliding action with its closed curved end (feature reference 8).

Operation of Invention

Figure 13:
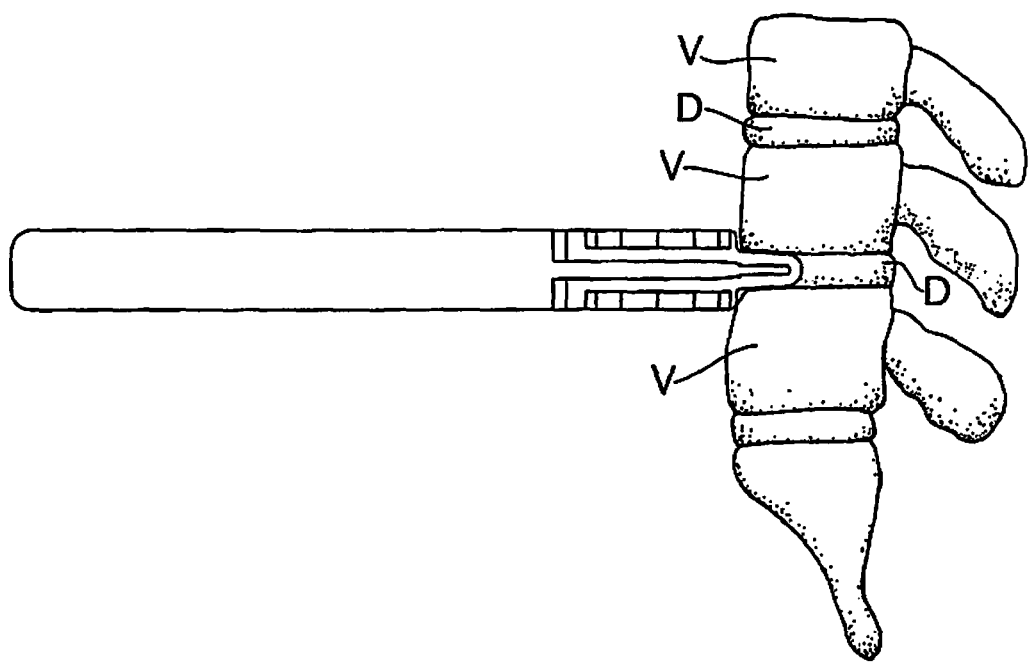
FIG. 13 is a side view of the of the spine with the distal tip of the retractor inserted in the disc space, with 'V' indicating vertebra and 'D' indicating the intervertebral disc.

The operation of the invention is described in the following paragraph in part referring to the abbreviated illustration in FIG. 13, which shows the lumbar spine and the retractor, with "D" indicating intervertebral disks and "V" indicating lumbar vertebra. The preferred application of the invention is detailed as follows:

The primary surgical procedures anticipated to utilize the invention at this time involve the lumbar spine, especially those concerning diskectomies at the L5-S1, L4-L5, L3-L4, and L2-L3 levels via a retroperitoneal approach anteriorly with retraction (Refer to FIG. 13). In reference to the most anticipated utilization, bilateral placement of the retractors (blades) is suggested, with placement to be as far to one side of the other initially as possible, after insertion of the distractor-retractor assemblies and subsequent initial removal of the distractors. This allows for maximal exposure to disk space while working on the other side.

It is preferred to initially remove some of the inner nucleus pulposus prior to insertion of the retractor/distractor assembly and initial distraction of the disk space, thereby eliminating the risk of pushing material into the spinal canal. In addition, during placement of the distractors in the disk space, it is also part of the preferred method to minimize the possibility of over distraction of the disk space, by distracting in a graduated fashion rather than trying to bring the disk space up to its maximal size immediately.

Generally, for the lumbar region, I would recommend starting out with an 8 mm distractor head with matching retractor initially, and then gradually increasing to the size desired via procedurally alternating the removal and insertion of retractor-distractor assemblies laterally. Coincident with these procedures, one must be careful when dealing with osteoporotic bone, so that one does not over distract, since this might create some risk of compression fractures or making divots in the bone which can make future placement of implants within the disk-space difficult. After the desired distraction is achieved, the distal tip of the retractor is left in the disk space during the remainder the operation allowing it to maintain distraction while providing a means for retraction (FIG. 13).

When the desired distraction is achieved with the distractor-retractor assembly, the progression of retraction may be continued or maintained with the flexible portion of the retractor while distraction is being maintained with the matching profile of the distal tip of the retractor.

Future Revisions

Anticipated revisions that are conceptual extensions of the above described preferred embodiment include, but are not limited to; an assembly that has distractor rod diameter and length changes, other methods of fastening the distractor head to the rod, changes in the variation of convexly curved surfaces (soft tissue interface), curve modifications to distractor head and retractor matching profiles, and size modifications involving differing proportions of several aspects of the assembly to enable use for posterior to anterior procedures from the lumbar to cervical regions of the spine. Additional possible revisions are listed as follows:

1. The thin flexible blade-like portion of the tool may be proportionally increased in length, while correspondingly shortening other prominent features like the keyway slot and its opposing surfaces to enable better use in other regions of the spine.

2. Distractor head surfaces may be modified with rasp surfaces to enable preparation of vertebral endplates for various implants and grafts for spinal fusion or disk replacements.

3. Distractor head matching profile available with differing thickness to enhance or augment other distractor head features.

3. Distractor head and distal tip of retractor modified to include a light source for better visualization of the operating field.

4. The shape of the retractor and/or distractor may be modified with formed or rectangular sections to accept commonly used implants and grafts for spinal fusion or disk replacement.

5. Retractor changes in the curvature surrounding the blade and the amount of the retractor which is solid versus flexible (thinned section).

6. Radio opacity to enable x-ray imaging while portions of the assembly are left in the operating site.

Future possible revisions will offer marked increases in the function and utility of the present invention over and above the current preferred embodiment. This is significant, considering that the current preferred embodiment offers important advantages in the surgical arena such as:

1. The direct placement of a retractor attached to a distractor to maintain soft tissue retraction without the need for an individual holding the retractor blade and maintaining pressure on the soft tissues, which provides the surgeon with additional control of the soft tissue retraction process.

2. A distractor retractor assembly that reduces the chances of soft tissue coming out from underneath the retractor due to the fact that a portion of the retractor extends down into the disk space. This is particularly important, since the migration of the soft tissue during spinal surgery should be minimized, since it could increase the chances for soft tissue damage during final removal of disk space material and/or placement of implants.

3. A retractor which has a proximal flexible portion, allowing one to bend this portion of the retractor away from the operating field, resulting in an increase of the amount of visual exposure and light that can be brought into the operating field, resulting in improved quality of the visual exposure at the operating site.

4. The integration of a distractor head with a retractor to provide maintenance of the disk height during removal of the disk material, which tends to collapse as the disk material is removed. This is possible since successive replacement of the distraction portion of the assembly is enabled via the keyway and slot on the retractor. This characteristic of the invention aids in the gradual progression of distraction in addition to allowing for greater visibility, thus improving access for the removal of any disk herniated fragments from behind the disk space.

5. Surgical distraction of vertebra and retraction of adjacent soft tissue can be maintained by the retractor after the distractor integrated with its retractor has accomplished initial distraction. Thus allowing subsequent removal of the distractor tool from the retractor keyway and the operating site after the initial distraction, providing retraction with a comparative increase in access to the operating site when distraction and retraction are coincident surgical requirements.

These are not the only conceivable advantages that the current embodiment offers, since the unique nature of the having a keyed distractor head attached to a rod, which offers the option to be integrated with a retractor—can offer other advantages based on emerging procedures that may call for its use.

In summary, when the preferred embodiment of the invention is utilized, it provides for the complete removal of the disk, removal of the vertebral cartilagonous end-plates in a safe fashion—protecting the soft tissue surrounding the disk, as well as maintaining distraction of the disk space, allowing one to do the most complete removal of the disk space and fragments that have herniated behind the vertebral body.

The invention claimed is:

1. A distractor retractor assembly for use in spinal surgery comprising:
a distractor retractor assembly including a distractor portion and a retractor portion, said distractor portion including a distractor head and a distractor rod, said distractor head having a distal end and a proximal end, said distractor rod is removably secured to said proximal end of said distractor head, said distal end of the said distractor head having a tapered profile between said distal end and said proximal end and being constructed and arranged for insertion between adjacent vertebral bodies, said distal head including a plurality of side faces positioned between said distal end and said proximal end,
a keyed shaped projection secured to one of said side faces, said retractor portion including a distal tip portion, a central portion, and a proximal portion, said distal tip also being proximate the same shape as said distractor head, said distal tip portion being constructed and arranged for insertion between adjacent vertebral bodies, said keyed shaped projection of said distractor head having a profile which is constructed and arranged to be received in a keyway to operatively connect said distractor portion and said retractor portion enabling insertion of said distractor retractor assembly between adjacent vertebral bodies
wherein said retractor portion is substantially the same length as the distractor portion,
wherein the keyway is configured with a beveled shape which enables the keyway to retain the distractor head.

2. The distractor retractor assembly of claim 1, wherein said keyway has a closed shape at its distal end, whereby said closed shape prevents said keyed distractor head from sliding in advance of said retractor portion when both said distractor portion and said distractor portion together are inserted into an operating site.

3. The distractor retractor assembly of claim 1, wherein said distractor rod enables an insertion force to be applied to said distractor head and thereby an insertion force is applied to said retractor through said keyway.

4. The distractor retractor assembly of claim 1, wherein said keyway prevents said distractor head from separating from said retractor portion when both said distractor portion and retractor portion together are inserted into an operating side with the insertion force applied to said distractor portion.

5. The distractor retractor assembly of claim 1, wherein said distractor rod enables a removal force to be applied to the distractor head and thereby remove the distractor head from said keyway and an operating site.

6. A distractor retractor assembly for use in spinal surgery comprising:
a distractor retractor assembly including a distractor portion and a retractor portion, said distractor portion including a distractor head and a distractor rod, said distractor head having a distal end and a proximal end,
said distractor head comprising a keyed shaped projection secured to the distractor retractor assembly, said keyed shaped projection of said distractor head having a profile which is constructed and arranged to be received in a keyway to operatively connect said distractor retractor assembly between adjacent vertebral bodies,
wherein the keyway is configured with a beveled shape which enables the keyway to retain the distractor head, and
wherein said retractor portion is substantially the same length as the distractor portion.

7. A distractor retractor assembly for use in spinal surgery comprising:
a distractor retractor assembly including a distractor portion and a retractor portion, said distractor portion including a distractor head and a distractor rod, said distractor head having a distal end and a proximal end, said distractor rod is removably secured to said proximal end of said distractor head, said distal end of the said distractor head having a tapered profile between said distal end and said proximal end and being constructed and arranged for insertion between adjacent vertebral bodies, said distal head including a plurality of side faces positioned between said distal end and said proximal end,
a keyed shaped projection secured to one of said side faces, said retractor portion including a distal tip portion, a central portion, and a proximal portion, said distal tip portion also being proximate the same shape as said distractor head, said distal tip portion being constructed and arranged for insertion between adjacent vertebral bodies, said keyed shaped projection of said distractor head having a profile which is constructed and arranged to be received in a keyway to operatively connect said distractor retractor assembly between adjacent vertebral bodies,
wherein said retractor portion is substantially the same length as said distractor portion.

8. The distractor retractor assembly of claim 7, wherein the retractor portion is substantially flat along a longitudinal length of the retractor portion.

9. The distractor retractor assembly of claim 8, wherein a portion of the retractor portion is convexly curved.

10. The distractor retractor assembly of claim 7, wherein a portion of the retractor portion is flexible to bend sufficiently to move soft tissue while remaining inserted between adjacent vertebral bodies.

11. The distractor retractor assembly of claim 7, wherein the distractor head is threadably engaged to the distractor rod.

12. The distractor retractor assembly of claim 7, wherein a distal end of the keyed shaped projection is round and is configured to match the distal end of the keyway.

* * * * *